(12) United States Patent
Herring

(10) Patent No.: US 7,701,578 B1
(45) Date of Patent: Apr. 20, 2010

(54) PLANAR MICRO-DISCHARGE GAS DETECTOR

(76) Inventor: Cyrus M. Herring, Caviton, Inc., 60 Hazelwood Dr., Suite 244, Champaign, IL (US) 61820

( * ) Notice: Subject to any disclaimer, the term of this patent is extended or adjusted under 35 U.S.C. 154(b) by 774 days.

(21) Appl. No.: 10/938,960

(22) Filed: Sep. 10, 2004

Related U.S. Application Data

(60) Provisional application No. 60/502,676, filed on Sep. 12, 2003.

(51) Int. Cl.
| | |
|---|---|
| G01N 21/25 | (2006.01) |
| G01J 3/30 | (2006.01) |
| G01J 3/443 | (2006.01) |
| G01T 1/18 | (2006.01) |
| G01T 1/185 | (2006.01) |
| H01J 47/00 | (2006.01) |
| G01N 21/00 | (2006.01) |

(52) U.S. Cl. ............ 356/417; 356/311; 356/313; 356/316; 250/374; 250/382; 250/385.1; 250/385.2; 422/82.05

(58) Field of Classification Search .......... None
See application file for complete search history.

(56) References Cited

U.S. PATENT DOCUMENTS

| | | | | |
|---|---|---|---|---|
| 3,798,502 | A * | 3/1974 | Ngo | 315/169.2 |
| 3,821,748 | A * | 6/1974 | Brown | 347/112 |
| 3,935,494 | A * | 1/1976 | Dick et al. | 313/587 |
| 4,100,447 | A * | 7/1978 | Tsui et al. | 313/582 |
| 4,109,146 | A * | 8/1978 | Hillman | 250/227.13 |
| 4,268,826 | A * | 5/1981 | Scott et al. | 345/183 |
| 4,433,354 | A * | 2/1984 | Lange et al. | 361/120 |
| 4,494,037 | A * | 1/1985 | de Vries | 313/584 |
| 4,494,038 | A * | 1/1985 | Wedding et al. | 313/587 |
| 4,783,651 | A * | 11/1988 | Fischer et al. | 345/71 |
| 5,438,343 | A * | 8/1995 | Khan et al. | 313/493 |
| 5,591,896 | A * | 1/1997 | Lin | 73/31.05 |
| 5,703,433 | A * | 12/1997 | Fujii et al. | 313/484 |
| 5,747,815 | A * | 5/1998 | Young et al. | 250/423 R |
| 5,909,280 | A * | 6/1999 | Zavracky | 356/454 |

(Continued)

FOREIGN PATENT DOCUMENTS

GB 1411804 A * 10/1975

OTHER PUBLICATIONS

U.S. Appl. No. 10/241,887, Cyrus M. Herring.

*Primary Examiner*—Tarifur Chowdhury
*Assistant Examiner*—Gordon J Stock, Jr.
(74) *Attorney, Agent, or Firm*—Summa, Additon & Ashe P.A.

(57) ABSTRACT

A micro-sized gas detecting device with two electrodes separated by a gap of width ranging from 1 to 500 microns, where the detection is based on emission spectroscopy of gases in an electric discharge across the gap (discharge region) as the gas flows through the region. The characteristic light emitted by molecules during the discharge can be detected directly with photodiodes or transferred through optical fiber and detected with remote optical sensing components. The device can have single or multiple discharge regions in an array so that light emitted can be monitored at different wavelengths simultaneously. The device can operate under gaseous pressure ranging from a few milli-Torr to a few atmospheres. The device consumes little power (50 mW-100 mW) and can be powered with an alternating current and has the potential to be battery powered.

14 Claims, 9 Drawing Sheets

U.S. PATENT DOCUMENTS

| | | |
|---|---|---|
| 5,955,886 A | 9/1999 | Cohen et al. |
| 6,194,833 B1 * | 2/2001 | DeTemple et al. .......... 313/631 |
| 6,353,324 B1 * | 3/2002 | Uber et al. ................. 324/457 |
| 6,457,347 B1 | 10/2002 | Koo |
| 6,828,730 B2 * | 12/2004 | Eden et al. .................. 313/538 |
| 6,836,262 B2 * | 12/2004 | Hashimoto et al. ............ 345/60 |
| 2004/0027068 A1 * | 2/2004 | Chien et al. ................. 313/581 |
| 2004/0245993 A1 * | 12/2004 | Bonne ....................... 324/464 |

* cited by examiner

PLANAR MICRO-DISCHARGE GAS DETECTOR

CROSS REFERENCE TO RELATED APPLICATION

This application claims the benefit of U.S. Provisional Application Ser. No. 60/502,676, Sep. 12, 2003.

FIELD OF INVENTION

This invention pertains to gas detection, especially for nitric oxide in exhaust gas, and gas chromatography detection and analysis.

BACKGROUND OF INVENTION

Nitric oxide (NO), along with the other hazardous nitrogen oxides, is known to be involved in and important to many physiologically or clinically important processes. It is also an increasing concern for its environmental impact. Nitric oxide is commonly produced as a byproduct in the combustion processes. Therefore, there is a substantial need for a gas detector that can provide real-time monitoring of nitric oxide, particularly in exhaust gas mixtures, in a sensitive, accurate and economic manner.

Gas chromatography is a scientific method of gas analysis and identification, including trace gas identification such as chemical agent detection. The most sensitive and differentiating gas detectors used in gas chromatography are also the most expensive and bulky. Thus there is the need for less expensive, lighter, highly sensitive and selective gas detectors for gas chromatography.

Gas analysis involves identification and quantification (measuring the partial pressure of each gas) when multiple gases are present in a mixture of gases. The basis of gas identification and quantification for the current invention is emission spectroscopy, which is identification of gases from characteristic light emitted from molecules or atoms. I have developed a nanoliter-sized gas discharge device which causes gases to emit light when they enter a small, high-electric field region. The light from the discharge can be detected by several instruments, including spectrometers (grating or prism based), photodiodes, vacuum photodiodes, and photomultiplier tubes; even the human eye can be used to identify some gases, such as the light emitted from neon (which is the same color emitted by neon signs).

My invention is a micro-discharge device (or an array of devices) through which gas may flow. Gases in the micro-discharge region emit light, which is detected with a photosensor. If there is an array of microdischarge devices, then each micro-discharge device in the detector array has at least one photosensor, and each photosensor may have an optical filter, making it sensitive for a particular wavelength range of interest. Gas may be forced to flow through the device from a pressure differential created by the gas source or from a pump.

Additionally, an electric circuit may be used to monitor the gas discharge characteristics such as a circuit for measuring the voltage or current across the discharge. This measurement can also be used to aid in gas identification since different gases typically have different electronic characteristics.

Fiber optics may be used to direct light from the discharge devices to the optical sensing equipment. My micro-discharge devices have the ability to withstand high temperatures such that they can be used directly in hot gas flow where optical sensing elements often fail to operate. Fiber optics would allow the detector to be located in a chemically reactive and high temperature environment while delivering the light to optical sensing equipment located a few centimeters to a few meters away in a relatively cool ambient atmosphere. This offers another advantage to my detector, that advantage being that little or no gas conditioning needs to be performed before an analysis is made. This speeds the analysis and reduces filtering and pre-conditioning costs.

THEORY OF OPERATION

Electric discharges can be formed in air if a voltage exists between two conductors creating an electric field which is in excess of 10 kV/cm. Often when discharges are formed in this manner in atmospheric pressure air, the discharge is erratic, forming thin, intense filaments that dance on the surface of the electrodes. It is known that the discharges become relatively stable if the product of gas pressure (P) and distance between electrodes (d) is several Torr*centimeters (Pd$\leq$Torr·cm), depending on the type and mixture of gases present. If the discharge is operated in an atmospheric pressure air environment, then the distance between electrodes must be $\leq$~100 microns ($10^{-4}$ meters). In my invention, the distance between electrodes is between 1 and 500 microns.

The electrodes can be made of metal or other conductor, and may be screen printed or patterned into substrates such as alumina, silicon, boron nitride, plastic, or other suitable insulator. At least two electrodes are needed to produce a stable micro-discharge, and they are typically separated by 100 microns or less, and are 100 microns wide or less. A power supply is connected to the conductors, and if the voltage between them creates an electric field >10 kV/cm, a discharge forms in the gas above the substrate and between the electrodes. In order to create a more durable discharge device, the metal electrodes can be coated with an insulator film such as magnesium oxide, silicon dioxide, or silicon nitride to prevent reactions between the gas and metal which can oxidize the electrodes. When an insulator film is covering the electrodes, the current applied to the electrodes must be alternating or continuously pulsed to sustain a discharge. Typical operating frequencies range from 10 kHz (10 kilohertz) to 10 MHz (10 megahertz), with the higher frequencies producing a more intense discharge.

An additional benefit to coating the electrodes with an insulating material and using alternating current to create a discharge is that the current delivered to the discharge is self-limiting. The discharge is composed primarily of negative electrons and positive ions. During each current pulse (½ of the alternating current cycle), negative electrons travel to the positive electrode and cover the insulating material with negative charge. Likewise, positive ions travel to the negative electrode and coat the insulating film with a positive charge. The build-up of charges on each electrode cancels the electric field between the two electrodes, and the discharge ceases. During the next ½ cycle of the current pulse, the process reverses, and the electrons and ions deposit on the opposite electrodes until an opposing field extinguishes the discharge. This type of discharge is referred to as a dielectric barrier discharge, and needs no external element in the power supply to limit current in the discharge, as is necessary in most direct current driven discharges. Multiple discharges can be made to operate on the same substrate all using a common power supply.

Once suitable conditions exist to form a discharge in the gas surrounding the electrodes, atomic and molecular optical radiation is produced. Each molecule or atom emits specific radiation which uniquely identifies that molecule or atom. If this light is analyzed appropriately, it can be used to identify species in the discharge. Additionally, the intensity of light depends on the partial pressure of species present in the discharge. Algorithms can be generated to determine the type and concentration of gases present in the discharge, which are also dependent on the electrical power supply operating characteristics (including frequency, voltage, and operating waveform).

Of particular interest for my invention is the emission spectrum of nitric oxide (NO). Nitric oxide has a strong emission band extending from 214 nm to 287 nm. This emission band has many strong peaks, any of which can be used for NO identification. The intensity of this emission is strongly influenced by other gases present in the discharge. In particular, oxygen ($O_2$) reduces the NO emission. However, if the oxygen concentration is known, then the NO concentration can be deduced from the NO peak intensity, or conversely, if the NO concentration is known, then the oxygen concentration can be calculated. Oxygen concentration may be determined by atomic oxygen emission from a triplet of lines around 777 nm, or 795 nm, or 823 nm. If the intensity of emission of lines of both atomic oxygen and molecular nitric oxide are measured, then both the concentration of oxygen and nitric oxide can be determined. Similar strategies can be used to determine the concentration of water vapor (from hydrogen oxide, OH, emission near 308 nm or 282 nm), and carbon monoxide (multiple lines between 209 nm to 240 nm). The concentrations of all these chemicals can be made simultaneously, with each measurement taking less than 100 ms (milliseconds). This is a great improvement over current technologies which require gas sampling and conditioning, which increase the time for taking measurements to several minutes.

The spectroscopic identification of gases present in a discharge often requires a relatively large, complex and expensive spectrometer to analyze the light from the discharge. If the gas composition is roughly known, then a more simple technique may be used to obtain concentration measurements, greatly reducing the cost of a piece of equipment. In this case, several strategic wavelengths of the emission spectrum are monitored using inexpensive photodiodes combined with interference filters to select the wavelength of interest. A planar, linear array of micro-discharge gas devices can be fabricated, with a mating array of photodiodes mounted such that each photodiode monitors an individual discharge. Each micro-discharge/photodiode pair can monitor a different spectral region, and the intensity outputs analyzed in a computer for concentration analysis. This technique would require 2 emitter/detector pairs for each gas monitored. In the case of NO, 4 emitter/detector pairs would be needed, 2 for NO, and 2 for oxygen. Since the micro-discharge device can handle high temperatures, fiber optics can be used (which can also handle high temperatures) to couple the light from the discharge devices to the photodiode arrays, thus creating a device which can be inserted into hot process gas streams.

Additional information may be obtained on the gas species within the discharge by observing the afterglow (light output) after the excitation source (current) is shut off. Some atoms and molecules continue emitting light for microseconds after the discharge ends. The length of time and the color of light given off is another signature of the gas species within the discharge and can also be used to gain insight to the quantity and type of gas in the discharge. Thus a repeated pulse of power may be applied to the discharge and light can be monitored not only during the main discharge but in the afterglow as well. Another way to observe the afterglow of the gas is to monitor light emission in the flow of gas downstream of the discharge. For instance, if the gas flow rate through the detector is 1 meter second (a typical flow rate), then light emission 1 mm downstream from the discharge serves as a point to observe the gas 1 millisecond after it exits the discharge region.

DETAILED DESCRIPTION OF INVENTION

I have designed a micro-discharge device that can be operated with an AC power supply in gases at pressure ranges from a few milli-Torr to a few atmospheres. The device has two electrodes typically separated by a gap of several tens of microns (the gap may be one micron to 500 microns). A discharge is formed in the gas in the gap by applying an AC voltage between the two electrodes.

In fact, it is the small size of the discharge that allows it to operate in a stable manner at atmospheric pressure. Larger dimension devices (greater than ~200 microns) tend to exhibit instability in the discharge which results in noise, limiting the sensitivity. Atmospheric pressure operation is an advantage since external pumps are not required as they are in several competing detector technologies.

If a pump is used, thus decreasing the operating pressure of the discharge, the optical radiation emitted from the discharge will have a reduced linewidth. This will allow the identification of more peaks within a given wavelength range, increasing the number of chemicals that can be simultaneously identified in the case where several chemicals are present in the discharge at the same time.

In operation at atmospheric pressure a typical device consumes around 10 mA at 180V in a helium gas. Thus, using only 1.8 watts, a small battery powered supply can keep the device working in excess of 24 hours.

A fiber-optic cable (or multiple fibers) can be inserted into holes drilled in the body of the detector to transmit light from the discharge to equipment (36), such as a spectrometer or photodiode for spectral analysis. In fact, an array of fibers (36a) in close proximity to the discharge can gather information about different parts of the discharge all at the same time. Optical fibers can be 5 smaller than one micron core diameter to larger than 100 microns. Since the discharge length is approximately 1 to 500 microns, optical fibers are of the proper size for use with the current invention. Fibers also have the property to filter light they collect. Thus proper choice of fiber diameter and material can serve as a filter to block light that is not of interest.

Figure 1:
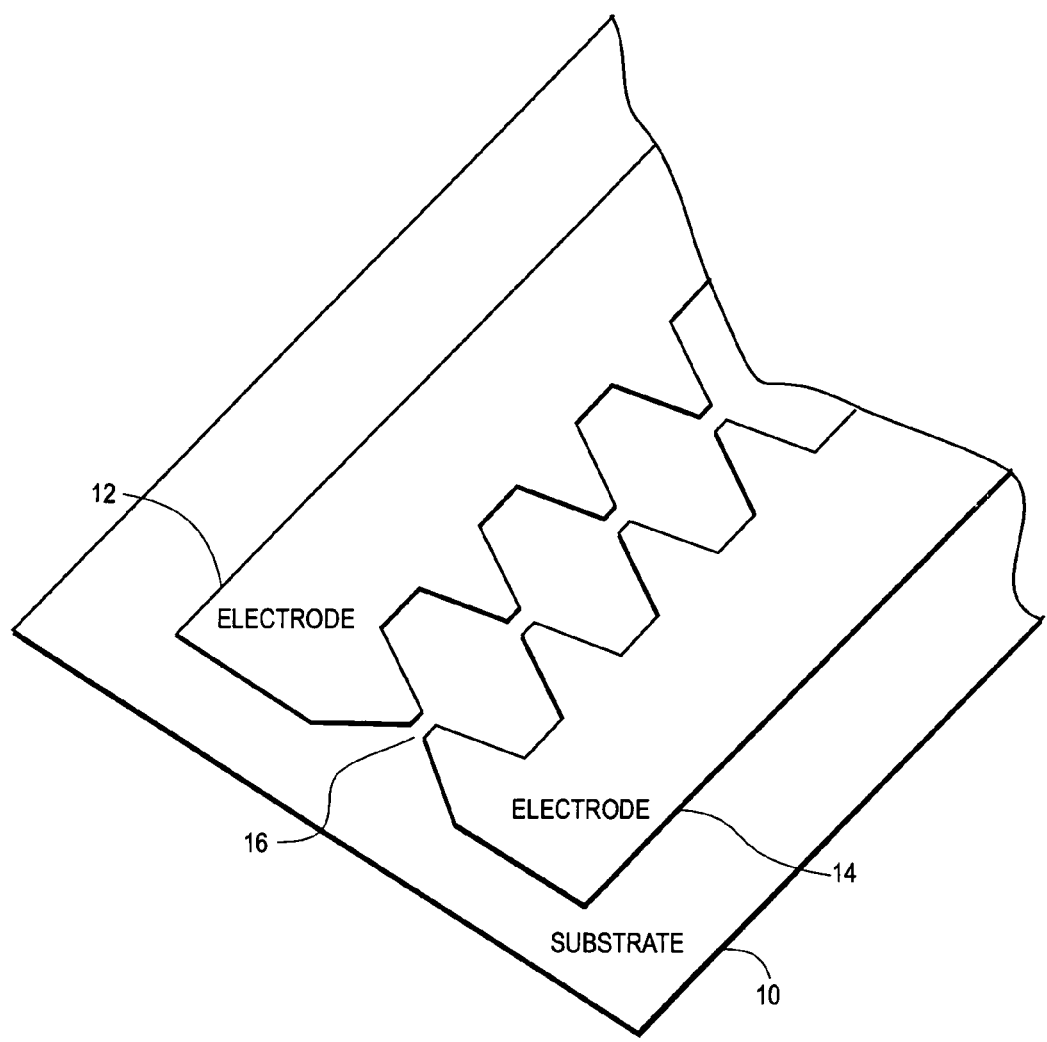
FIG. 1 shows the basic structure of the preferred embodiment of the device. The substrate (10) is made of any insulating material, including silicon, silicon nitride, silicon carbide, glass, mica, ceramic, quartz, or even plastic. This substrate can be any thickness and in general provides support for the electrodes (12) and (14). The figure was drawn assuming ½ millimeter thickness. The electrodes can be made of any conductor, but materials that have good adhesion to the substrate are desired. The electrodes can be vacuum deposited, electroplated, screen printed, or attached to the substrate with adhesives. The electrodes (12) and (14) can be formed initially as a continuous sheet of metal on the substrate and subsequent manufacturing steps can remove the unwanted metal to form the desired shape. The metal may have different compositions adjacent to the substrate to promote adhesion. The total metal thickness can range from 100's of angstroms to 100's of microns. Electrodes (12) and (14) have at least one region where the metal from each are relatively close to one another. The gap between them may be from 1 to 100's of microns, and this gap is referred to as the discharge region (16), a region of intense electric field when a voltage difference is applied between the electrodes. The width of the gap is also from 1 to 100's of microns. The device may have one such region, or many parallel devices, 4 are shown in the figure. Several features are not shown on FIG. 1. One important design is an insulative coating applied over the entire surface of the device. This coating enables each discharge region to operate as a dielectric barrier discharge, such that many devices can work in parallel. Also, a means for supplying an AC voltage between electrodes (12) and (14) is not shown. This voltage should be sufficient to cause a breakdown of the gas in the discharge region, anywhere between 100 to 1000 volts or higher, and at frequencies of 1 hertz to 10 megahertz.
Figure 2:
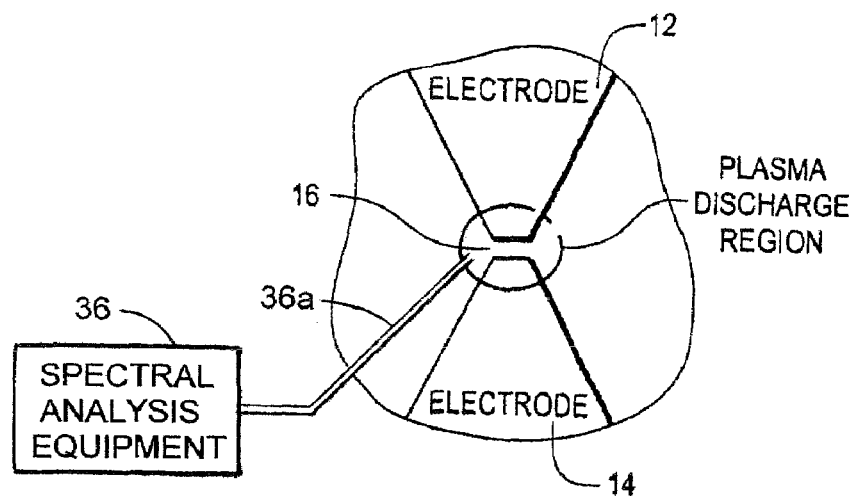
FIG. 2 shows a close-up top view from above the discharge region (16). The circle shown represents a typical boundary of the gas discharge when little or no gas flow is present.
Figure 2A:
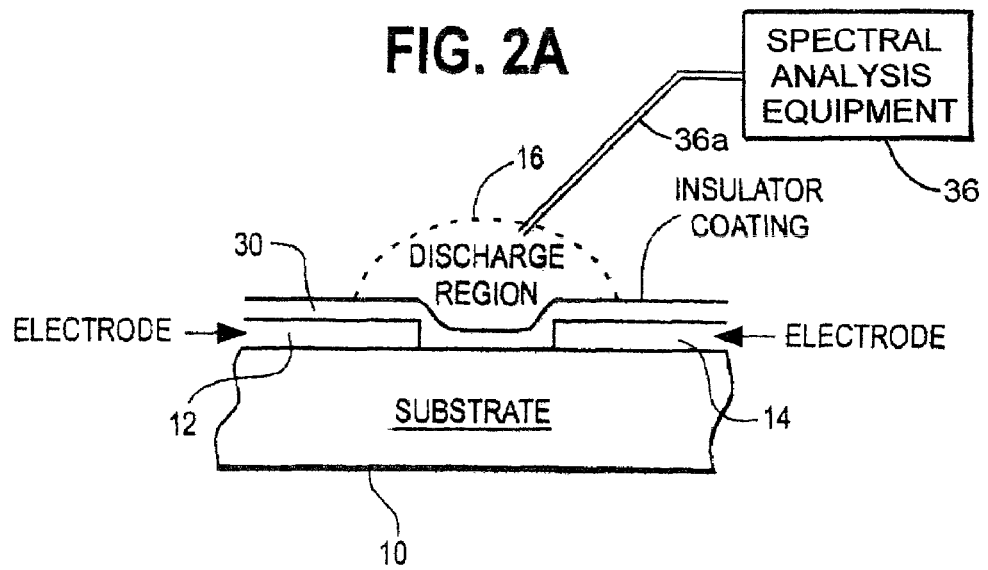
FIG. 2a shows a cross-sectional view of the discharge region (16), with the insulative coating shown (30). The dotted curve represents how the discharge region (16) may extend above the surface of the device.
Figure 3:
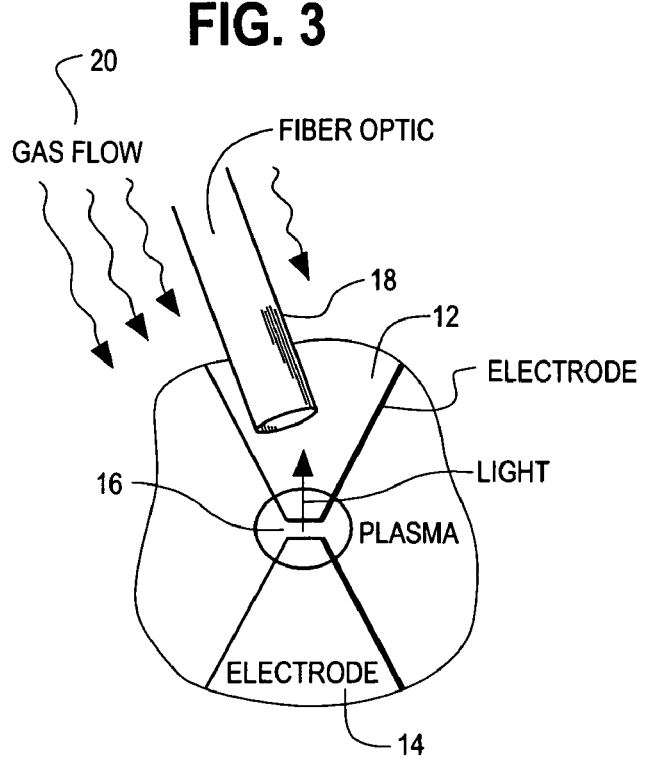
FIG. 3 shows another close-up top view of the discharge region (16), with a fiber optic cable (18) shown which collects the light from the discharge. The fiber would typically be positioned up-stream of the gas flow (20) in order to help prevent deposits from forming on the face of the fiber.
Figure 3A:
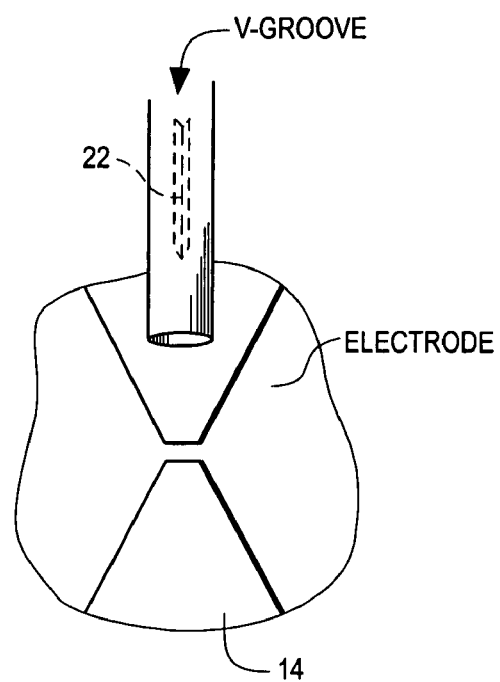
FIG. 3a further shows how a "V-groove" (22) may be used to facilitate fiber positioning near the discharge region. The fiber can be mechanically held in the V-groove (22) or bound to the surface in some other fashion.
Figure 4:
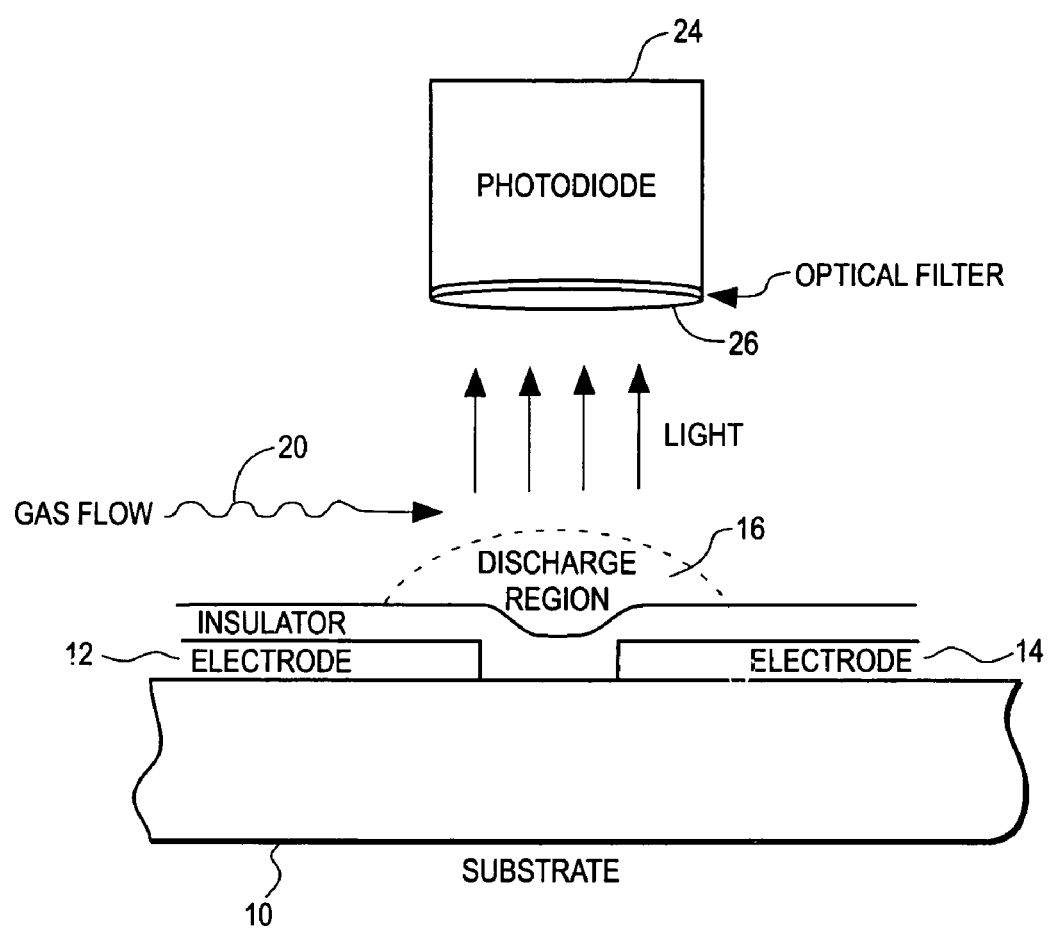
FIG. 4 shows an alternative way of collecting the light from the discharge. In this figure, a photodiode (24) is positioned near to the discharge device. Ideally, there would be at least two photodiodes collecting light from each discharge in the device in order to decrease noise signals caused by fluctuations in discharge intensity created by power supply fluctuations. Additionally, an optical filter (26) may be added between the photodiode (24) and discharge region (16) to selectively filter particular portions of the spectrum for analysis. Ideally, each discharge would have a different color filter installed in front of the photodiode (24) for wavelength discrimination. Additionally, gas flow would be directed to help keep deposits from forming on the optical surface of the photodiode.
Figure 5:
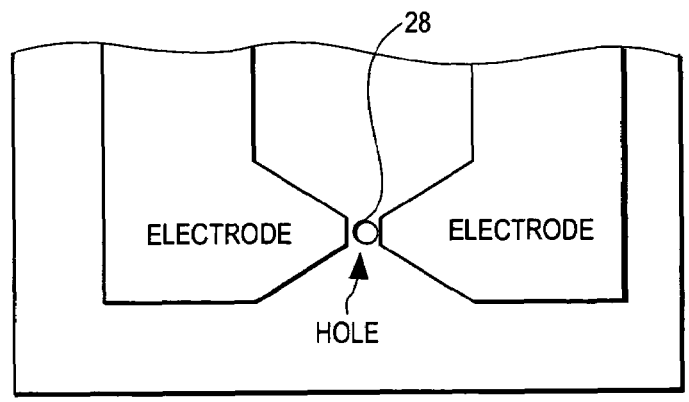
FIG. 5 shows a top view of an alternative geometry for device construction. In this case, a hole (28) is made through the substrate (1) just below the discharge region (16). Gas flow may be zero, or either direction through the hole. In this case, the light detection equipment may be on either side of the hole.
Figure 5A:
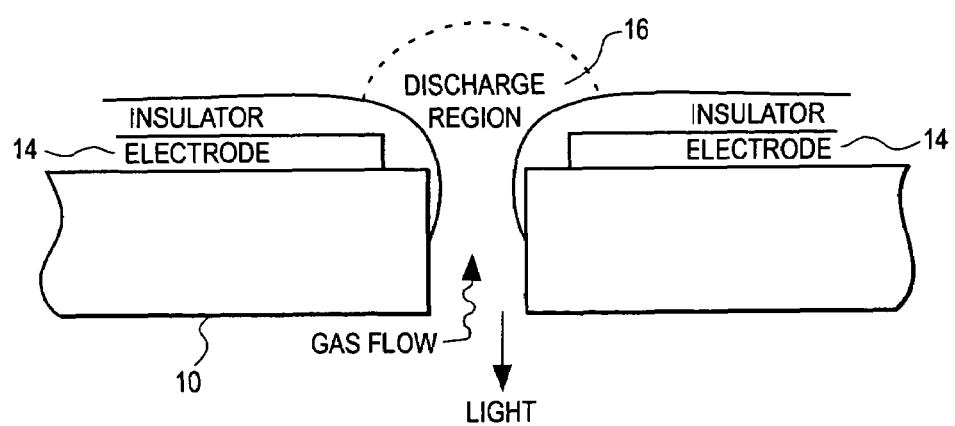
FIG. 5a shows a cross-sectional view of the alternative geometry in FIG. 5.
Figure 6:
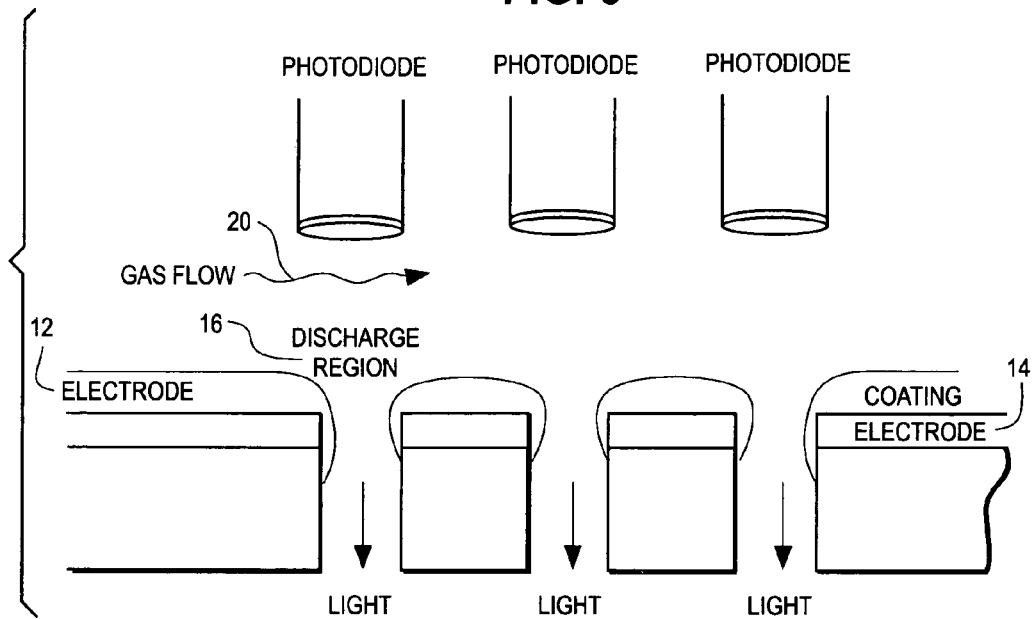
FIG. 6 shows a cross-sectional view of an embodiment with multiple holes (28) in the substrate. In this case, if there were a gas flow across the holes, then each hole would "view" the gas at a specific time after it exited the discharge. The holes away from discharge would only see light from the afterglow of the discharge and could give additional information to gas composition.
Figure 6A:
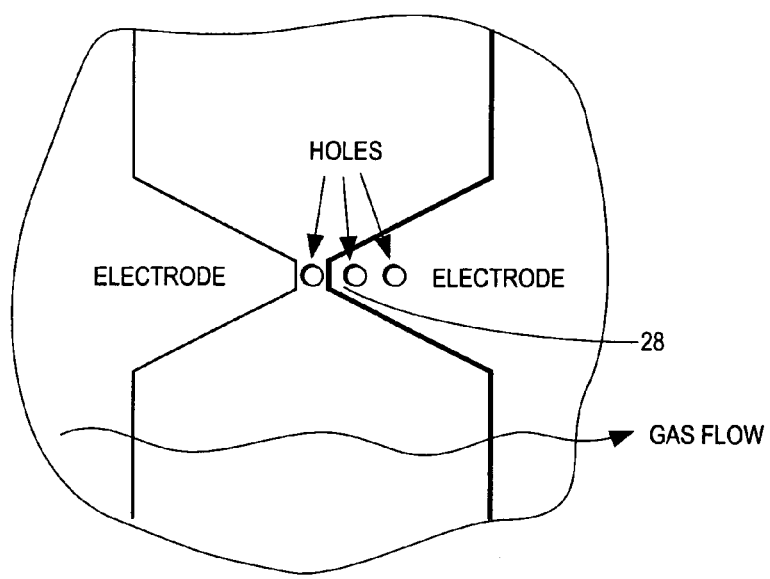
FIG. 6a shows a top view of the embodiment in FIG. 6.
Figure 7:
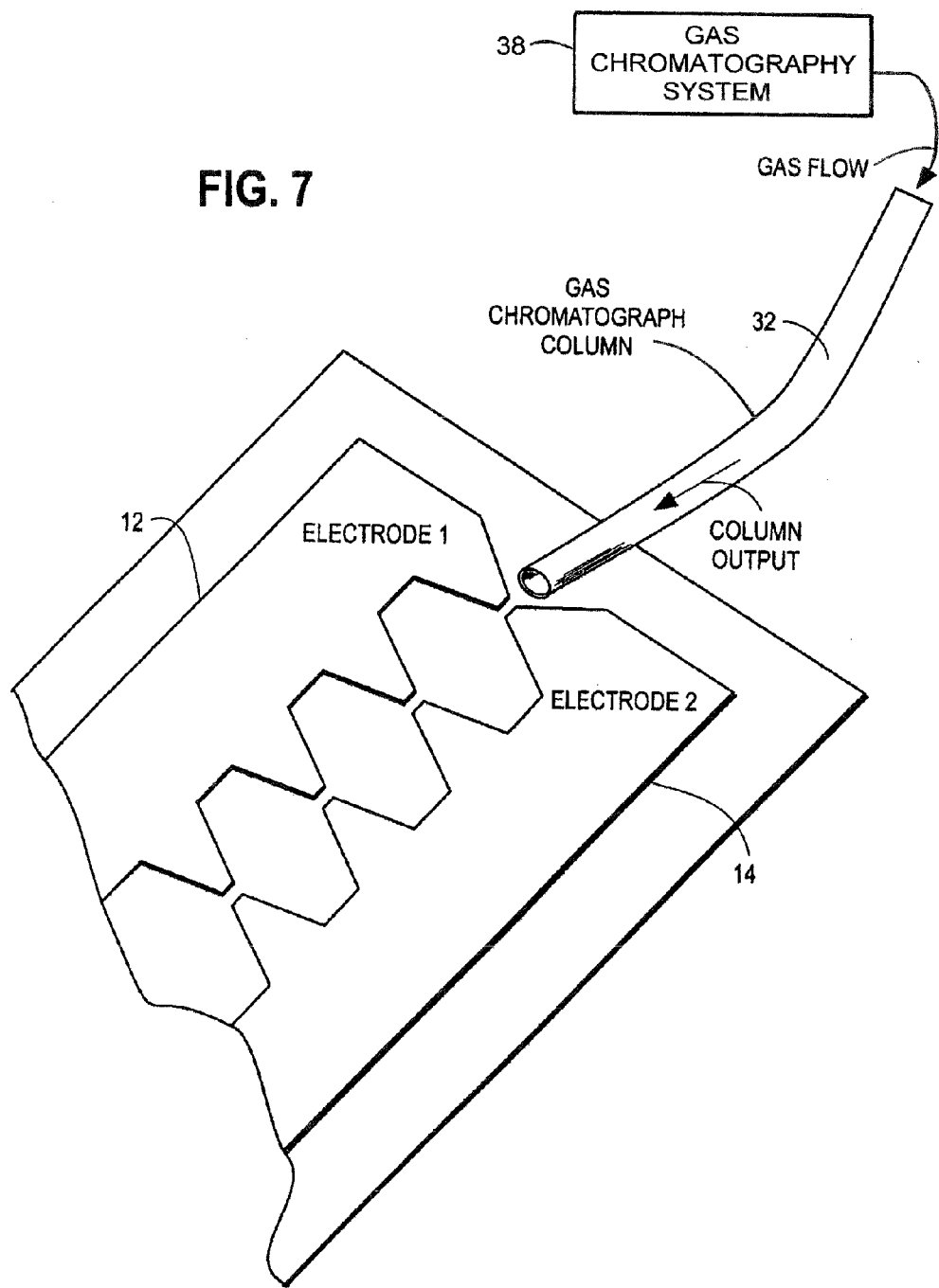
FIG. 7 pictures the device used as a gas detector for the gas coming from a small tube, such as the output of a gas chromatograph column (32). Here, the gas flows from the column and across one or multiple gas discharge devices, each giving off light which can be used for gas identification and quantification. Ideally, the column would also be miniaturized creating a complete detector which could be battery powered and portable. A benefit of using this detector technology with gas chromatography is not only the sensitive technique of determining when a gas exits a column, but the ability to identify the gas after it exits the column based on its emission spectrum. This ability greatly enhances the usefulness and power of gas chromatography systems (38).
Figure 8:
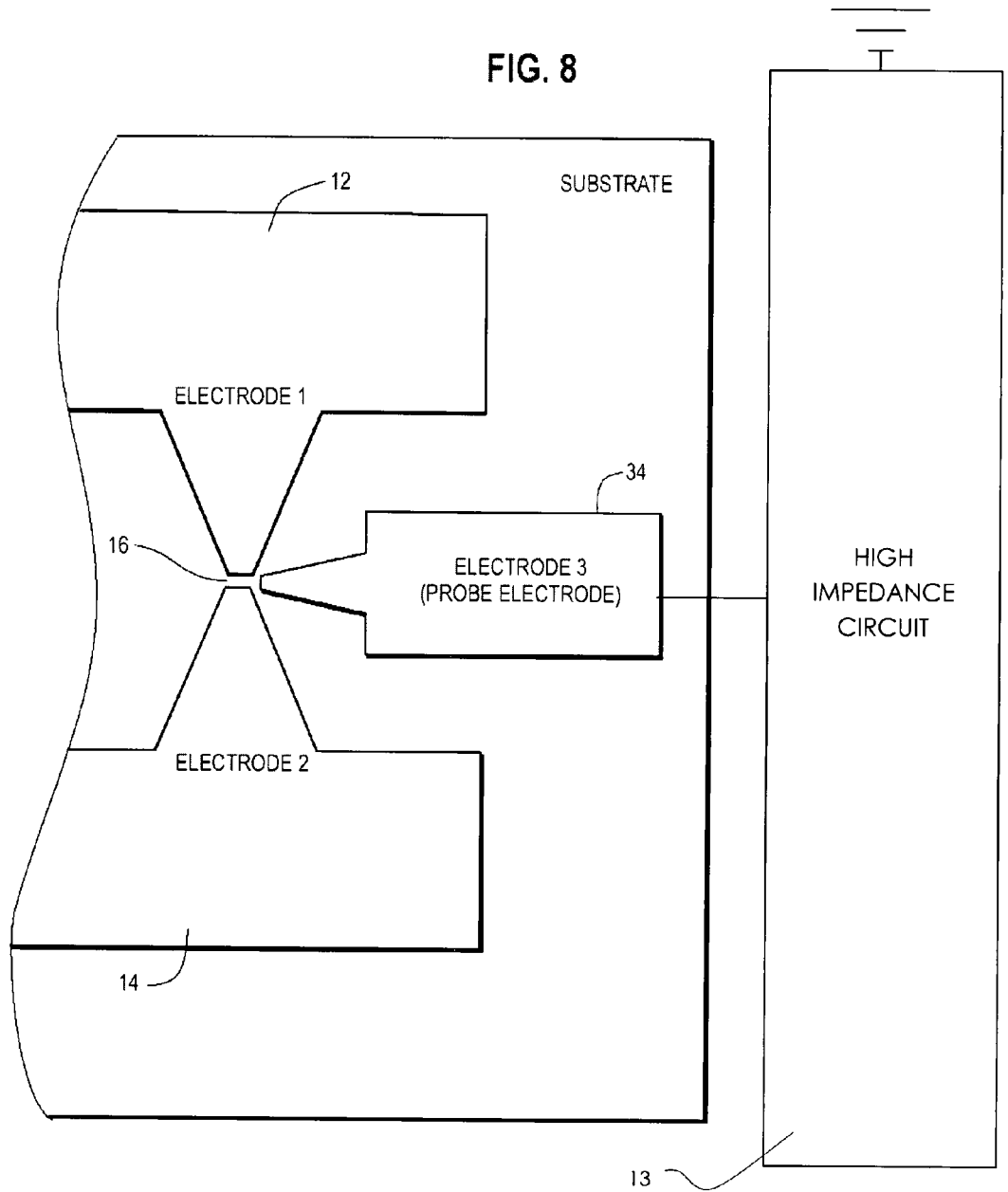
FIG. 8 shows the basic detector with an additional electrode. This probe electrode (34) serves as a probe to monitor the discharge characteristics. In operation, the electrode would be in direct contact with the plasma in the discharge region (16) (no insulator material) and would reach a potential which would depend on the operating characteristics of the plasma. The potential of this "sense" electrode would have an AC component with the same frequency as the discharge, but the average value will be different as different gases enter the discharge. A high impedance circuit (13) connected to the probe electrode (34) would measure the potential between the probe electrode (34) and a ground as an additional means for gas identification.
Figure 9:
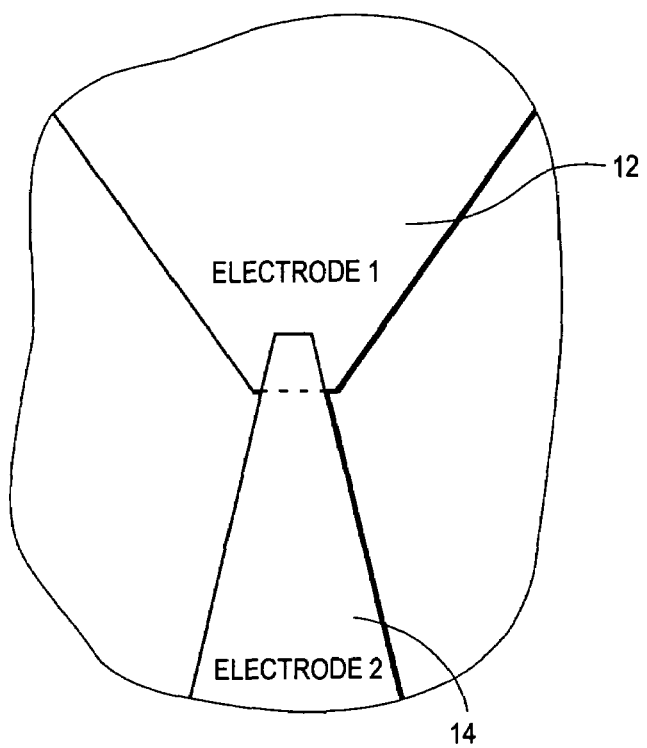
FIG. 9 shows a top view of one final geometrical arrangement of the electrodes. In this figure, electrode (12) and electrode (14) are overlapping but with an insulator (30) between the electrodes.
Figure 9A:
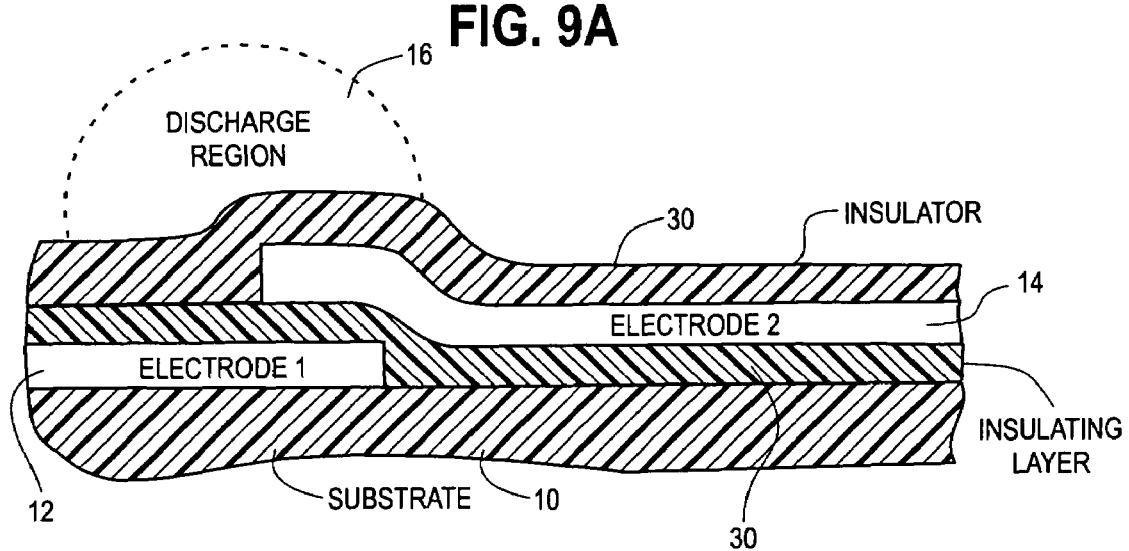
FIG. 9a shows a cross-sectional view of the geometric arrangement in FIG. 9. The electrodes (12) and (14) and insulator (30) all rest on a substrate (10). This overlapping design will create a stronger electric field which will facilitate discharge initiation in the discharge region.

I claim:

1. A gas discharge detector that analyzes a gas comprising:
   a) a substantially uniform, uninterrupted insulative substrate with a first surface;
   b) a first electrode on said first surface of said substrate;
   c) a second electrode positioned on said first surface such that said first and second electrodes define a gap of 1 to 500 microns between said electrodes and across said first surface;
   d) an insulative coating over a surface of said electrodes;
   e) the gas discharge detector adapted to receive sufficient voltage between said electrodes in the presence of a gas that causes the gas to emit light in a discharge region around the gap; and
   f) spectral analysis equipment that collects the light from the discharge region and that identifies properties of the gas from the light.

2. The detector of claim 1 wherein said spectral analysis equipment is a spectrometer that determines the identity or concentration of a component of the gas present in the discharge region.

3. The detector of claim 2 further comprising an optic fiber cable with a tip of said cable disposed near the discharge region that transmits the light to said spectral analysis equipment.

4. The detector of claim 3 additionally comprising a means for positioning a tip of said fiber cable near the discharge region.

5. A gas discharge detector that identifies properties of a gas sample in conjunction with a gas chromatography system, the detector comprising:
   a) a substantially uniform, uninterrupted insulative substrate with a first surface;
   b) a first electrode on said first surface of said substrate;
   c) a second electrode on said first surface of said substrate and disposed across said first surface from said first electrode to define a gap of 1 to 500 microns between said first and second electrodes;
   d) an insulative coating over a surface of said electrodes;

e) the gas discharge detector adapted to receive sufficient voltage between said electrodes in the presence of a gas that induces a light emitting gas discharge in a discharge region around the gap;
f) means for collecting light disposed sufficiently proximate the discharge region to collect light from the gas discharge; and
g) spectral analysis equipment that identifies properties of the gas emitted from the gas chromatography system by analyzing the light from the discharge region.

6. A gas discharge detector that analyzes a gas comprising:
a) a substantially uninterrupted insulative substrate with a first surface;
b) a first electrode on said first surface of said substrate;
c) a second electrode positioned on said first surface such that said first and second electrodes define a gap between said electrodes and across said first surface;
d) an insulative coating over a surface of said electrodes;
d) wherein the gas discharge detector is adapted to receive sufficient voltage between said electrodes on said first surface in the presence of a gas that causes light to be emitted in a discharge region around the gap; and
e) spectral analysis equipment that identifies properties of the gas by analyzing said light collected from the discharge region.

7. A gas discharge detector according to claim 6, further comprising an optical fiber cable that collects light emitted from a gas discharge and that transmits the light to the spectral analysis equipment.

8. A gas discharge detector according to claim 6, wherein said electrodes are positioned between 1 and 500 microns apart on said first surface.

9. A gas discharge detector according to claim 6, wherein an alternating current is applied to said electrodes.

10. A gas discharge detector according to claim 6, wherein said substrate comprises an insulating material selected from the group consisting of silicon, silicon nitride, silicon carbide, glass, mica, ceramics, quartz, or a plastic.

11. A gas discharge detector according to claim 6, further comprising a probe electrode located on said first surface of said substrate proximate the discharge region, wherein said probe electrode measures electrical properties of a gas discharge to identify gases therein.

12. A gas discharge detector that identifies properties of a gas, the detector being adapted to receive sufficient voltage between electrodes that causes light emitting gas discharge in a discharge region between the electrodes, the gas discharge detector comprising:
a) an insulative substrate with a first surface and a second surface;
b) a first electrode on said first surface of said substrate;
c) a second electrode positioned on said first surface across from said first electrode, wherein said substrate defines a hole between said electrodes, the hole extending through said substrate from said first surface to said second surface, wherein the light from the gas discharge is extracted from the hole and transmitted to
d) a light emission spectrometer that identifies the gas in the gas discharge.

13. A gas discharge device according to claim 12, wherein the light is collected from the end of the hole closest to said second surface of said substrate, opposite said electrodes.

14. A gas discharge detector that analyzes a gas, comprising:
a) a substantially uninterrupted insulative substrate with a first surface;
b) a first electrode on said first surface of said substrate;
c) an insulating layer on a portion of said first electrode and a portion of said substrate;
c) a second electrode positioned on said insulating layer such that said first and second electrodes extend over a common section of said substrate and are separated by said insulating layer;
d) wherein the gas discharge detector is adapted to receive sufficient voltage between said electrodes in the presence of a gas that causes light to be emitted in a discharge region around the electrodes; and
e) spectral analysis equipment that identifies properties of the gas by analyzing said light collected from the discharge region.

* * * * *